(12) United States Patent
Tadin et al.

(10) Patent No.: US 7,346,998 B2
(45) Date of Patent: Mar. 25, 2008

(54) FOOT MEASURING METHOD

(75) Inventors: Tony Tadin, Woodside, CA (US);
Arjen Sundman, Lake Oswego, OR (US)

(73) Assignee: Amfit, Inc., Vancouver, WA (US)

( * ) Notice: Subject to any disclaimer, the term of this patent is extended or adjusted under 35 U.S.C. 154(b) by 0 days.

(21) Appl. No.: 11/354,697

(22) Filed: Feb. 15, 2006

(65) Prior Publication Data
US 2006/0225297 A1 Oct. 12, 2006

Related U.S. Application Data

(60) Provisional application No. 60/653,026, filed on Feb. 15, 2005.

(51) Int. Cl.
*G01B 7/28* (2006.01)
*A61B 5/103* (2006.01)

(52) U.S. Cl. ...................................................... 33/515

(58) Field of Classification Search ................. 33/515, 33/514.2, 561.1
See application file for complete search history.

(56) References Cited

U.S. PATENT DOCUMENTS

| | | | |
|---|---|---|---|
| 2,330,317 A * | 9/1943 | Stewart ....................... 33/3 A |
| 4,449,264 A | 5/1984 | Schwartz ...................... 12/1 R |
| 4,454,618 A | 6/1984 | Curchod .......................... 12/1 |
| 4,517,696 A | 5/1985 | Schartz ............................ 12/1 |
| 4,876,758 A | 10/1989 | Rolloff ...................... 12/142 N |
| 4,936,560 A * | 6/1990 | Barozzi ....................... 269/266 |
| 5,640,779 A | 6/1997 | Rolloff ....................... 33/514.2 |
| 5,941,835 A | 8/1999 | Sundman ..................... 600/592 |
| 5,979,067 A * | 11/1999 | Waters ......................... 33/512 |
| 6,160,264 A * | 12/2000 | Rebiere ................. 250/559.22 |
| 6,864,687 B2 | 3/2005 | Walker ........................ 324/452 |
| 6,904,692 B2 * | 6/2005 | Tadin ............................ 33/515 |

* cited by examiner

*Primary Examiner*—Christopher W Fulton
(74) *Attorney, Agent, or Firm*—Ohlandt, Greeley, Ruggiero & Perle L.L.P.

(57) ABSTRACT

There is provided a foot measuring system that includes a support surface for a foot, a plurality of movable measurement structures, an inflatable diaphragm for contacting the first end of each structure and forcing a movement of each structure from an initial position toward a measurement position, a measurement device for measuring the measurement position relative to the initial position of each structure, after the movement of each structure, to determine a shape of the foot. Each structure of the plurality of movable structures has a first end and a second end. The present invention also includes a method for measuring the contours of a foot.

21 Claims, 3 Drawing Sheets

FOOT MEASURING METHOD

CROSS-REFERENCE TO RELATED APPLICATIONS

The present application is claiming priority of U.S. Provisional Patent Application Ser. No. 60/653,026, filed on Feb. 15, 2005, the content of which is herein incorporated by reference.

BACKGROUND OF THE INVENTION

1. Field of the Invention

The present invention relates to measurement devices and methods, and more particularly, to devices and methods for foot contour measurement.

2. Description of the Related Art

Foot contour measurement methods typically consist of sampling the surface of the foot using either mechanical (such as plaster et al.), electronic, electromechanical or electro-optical means.

A preferred device is manufactured by the assignee of this application. The same also holds a number of patents covering various methods to measure feet and to fabricate a custom machined insoles for the foot. One such device, a "Contact Digitizer", uses regularly spaced gauge pins that are urged upwards under the subject foot, as disclosed in U.S. Pat. Nos. 4,449,264, 4,454,618, 4,517,696, 4,876,758, and 5,941,835. These gauge pins are measured for position relative to a datum surface that is then processed to produce a digital model of the undersurface of the foot. This device is preferred over other technologies due to the ability of the gauge pins to deflect the soft tissue encountered when upwardly urged against the undersurface of the foot. The machine therefore makes allowances for the areas of the foot with soft tissue or where there may be underlying bone structure. This produces a data set which incorporates these allowances. When this data is used to produce a support for the foot, a more effective device is produced.

It is also possible to design electromechanical contour sampling devices with variations like an array of trailing swing arms that translate in one axis while measuring the position of the swing arms to determine the shape of the subject surface.

Such devices have been successfully applied worldwide for the measurement of the foot for the fabrication of custom foot support appliances (foot orthotics).

Prior art devices used gauge pins which were urged upwards against the undersurface of the foot by a pneumatically actuated diaphragm. The foot is placed against the top of the device and a device is slide under the toes to restrict the upwards force of the gauge pins under said toes.

The gauge pins are urged up by a diaphragm until they contact the undersurface of the foot. A separate mechanism is used to "lock" or freeze the gauge pins at the height attained. At this time the subject foot could be removed from the device. The gauge pins would retain the shape of the undersurface of the foot. A measurement means or measurement mechanism was used to determine the relative heights of the gauge pins. The resulting values were saved in a processor for storage and possibly subsequent manipulation and ultimately used to direct the operation of a robotic milling machine to produce the finished custom insole.

The prior art devices therefore required the following steps involved in the measurement of a foot: 1) place the foot on the device, 2) center the foot on the device using an incorporated heel guide, 3) slide the toe plate into position to restrict upwards motion of the gauge pins against the toes, 4) activate the diaphragm to urge up the gauge pins, 5) activate the locking mechanism once the gauge pins have contacted the subject foot, 6) remove the subject foot, 7) activate the measurement mechanism to determine the relative heights of the gauge pins, and deactivate the locking mechanism and the diaphragm to reset the gauge pins for the next measurement. Each of the steps must be repeated for each foot.

The prior art measurement mechanisms consisted of two measurements of the gauge pins in opposite directions. The processor uses these two measurements to determine an average value. It has been determined that the differences in these two measurements is so small as to be of little accuracy value. And by only measuring the gauge pins in one direction, at least 50% of the time used in measuring the gauge pins can be saved. It has also been determined that the measuring time can be further reduced by simply speeding up the scanning process. This reduction in scanning time eliminates the need for a locking mechanism.

The locking mechanism was a requirement in the prior art design due to a number of factors. The measurement mechanism was fairly slow and there was a risk of foot movement during the measuring process. Also, because it was desired to make a very accurate device, it was determined that for complete accuracy of gauge pin position, the pin must be locked in place at some point in time and then measured.

If the measurement could be done faster, then there is less risk of foot movement during the scan. By changing some of the measurement techniques, the scan time can be reduced by approximately 70%.

It is desirable to apply this technology to a broader market than simply in the medical applications where it is used presently. Prior art devices, however, do not lend themselves well to the broader (retail) market. The device is moderately fragile (each gauge pin can be sheared off) and the top surface is subject to damage by accidental spillage of liquids seeping into the interior of the device.

There is a need to provide contour sampling technology to a broader market than simply in the medical applications where it is used presently.

There is also a need to reduce the number of operator actions required to measure a foot to improve the simplicity of a contour sampling device.

There is a further need to enhance the prior art devices with new and unique improvements to address these shortcomings.

There is yet a further need to eliminate the need for a locking mechanism or the need for a toe plate.

There is also a need to eliminate the concern for device contamination and resulting failure due to contaminants being introduced through the top surface of the device.

SUMMARY OF THE INVENTION

The present invention includes a system and method, including a contour measurement device, for measuring the contour of an object, preferably a foot. The foot measuring system includes a support surface for a foot, a plurality of movable measurement structures, an inflatable diaphragm for contacting the first end of each structure and forcing a movement of each structure from an initial position toward a measurement position, a measurement device for measuring the measurement position relative to the initial position of each structure, after the movement of each structure, to determine a shape of the foot. Each structure of the plurality of movable structures has a first end and a second end.

The present invention also includes a method for measuring the contours of a foot. The method includes placing the foot against a support surface of a foot measuring system, inflating a diaphragm to force a plurality of movable measurement structures through the surface and toward the foot, moving each structure due to contact between the first end of each structure and the diaphragm, detecting a change in position of each the structure relative to an initial position of each the structure, and measuring a shape of the foot based upon the change in position of each the structure. Each structure of the plurality of movable structures has a first end and a second end, and each structure is limited in movement by contact between the second end and the foot.

The present invention also comprises a protective diaphragm to render the contour sampling device immune to contamination through the top of the device.

DESCRIPTION OF THE INVENTION

Figure 1:
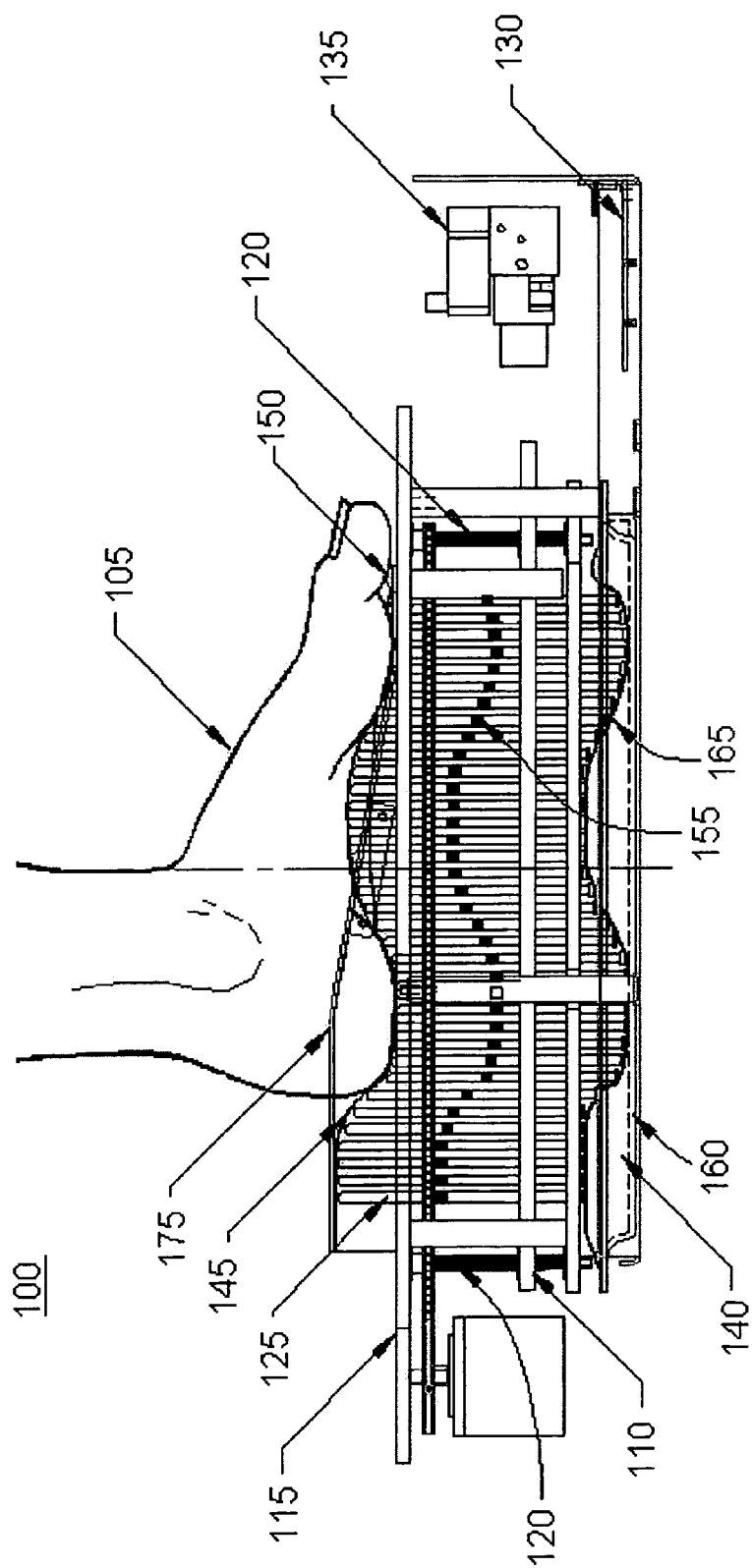
FIG. 1 is a side view of a system for measuring the contour of an object.

The present invention provides a foot measuring system that includes a support surface on which a foot is placed, a plurality of movable measurement structures each having a first end and a second end, an inflatable diaphragm for contacting the first end of each the structure and forcing a movement of each structure from an initial position toward a measurement position, and a measurement device for measuring the measurement position relative to the initial position of each the structure, after the movement of each the structure, to determine a shape of the foot.

In a preferred embodiment, the structures are elongated gauge pins oriented in a direction perpendicular to a plane of the support surface. The support surface includes a plurality of holes through which the second end of each of the structures can be advanced toward the foot in response to the upward pressure exerted by the inflated diaphragm.

In another preferred embodiment of the present invention, the gauge pins are measured by an array of electrostatic sensors that can sense the relative positions of an embedded metalized area on each gauge pin. These electrostatic sensors are mounted as a group on a circuit board with each sensor located at each gauge pin. This circuit board is moved in a direction corresponding to the lengthwise direction of the gauge pins. When the electrostatic sensor encounters the metalized area on a gauge pin, the relative position of each pin is determined. The relative position, or measurement position is determined by the distance traveled by the circuit board along each gauge pin until the sensor at each gauge pin detects the metalized area. This distance will vary at each gauge pin, resulting in an array of values representing the shape of the foot.

The diaphragm is preferably connected to a bottom surface of the measurement system to form an airtight cavity between portions of the diaphragm and the bottom surface. An air controller is connected to the cavity to controllably introduce air into the cavity to force the gauge pins upward toward the foot.

The system also includes a processor for controlling the air controller, the circuit board and sensors, and for at least retrieving measurement information. The processor may also be utilized to build a digital representation of the shape of the foot based on the measurement information. In one embodiment, the processor determines the initial position of each the structure prior to inflating the diaphragm, inflates the cavity, compares the initial position of each the structure with the measurement position of the each the structure after the diaphragm is inflated and each the structure stops moving do to restrictions caused by the inflated diaphragm and by the foot.

Embodiments of certain aspects of the measurement system, such as embodiments of the circuit board and gauge pins, are described in U.S. Pat. No. 5,640,779 to Rolloff et al., and U.S. Pat. No. 5,941,835 to Sundman, both of which are incorporated in their entirety by reference herein. Other embodiments of the circuit board and gauge pins are described in U.S. Pat. No. 6,864,687 to Walker et al., which is incorporated in its entirety by reference herein.

The system also preferably includes a protective diaphragm located at or near the surface that prevents contamination of the system through the top of the system when the foot is placed on the surface, yet does not restrict the movement of the plurality of structures beyond the surface. In a preferred embodiment, the contour sampling device of the present invention has incorporated therein a diaphragm disposed about the top of the unit between the gauge pins and the subject foot. The protective diaphragm is preferably made from a stretchable and flexible material. This diaphragm may be mounted to a liquid shedding frame.

In order to reduce the likelihood that any restriction on the gauge pin exists as a result of the protective diaphragm, the protective diaphragm's frame can be mounted above the top surface of the unit. This mounting distance is a significant fraction of the dynamic range of the gauge pins. In a preferred embodiment this distance is in the range between about 3-30 mm.

A toe plate may also be included, which is a device that is slid under the forefoot, typically forward of the ball of the foot to prevent the toes from being pushed up by the gauge pins. While a device such as a toe plate that selectively restricts the upward motion of the gauge pins can be diagnostically useful, its placement requires some care and may therefore be undesirable in a measurement device for the retail market.

In an alternate embodiment, the need for a toe plate has been eliminated by placing the toes purposely off the end of the array of gauge pins. Pin locations are further tailored to prevent unnecessary upwards motion of the toe end of the foot. To assist the user in positioning the foot, a ridge of material in a shape designed to be similar to the shape of the transverse sulcus of the foot is provided. When the foot is placed against the top of the scanner, the toes are positioned forward of this ridge with the ball of the foot behind it. All areas behind the ridge will be periodically sampled by the gauge pins.

The present invention also provides a method for measuring the contours of a foot. The method includes placing the foot against the support surface of the foot measuring system, and inflating the diaphragm to force the plurality of movable measurement structures, such as the gauge pins, through the surface a toward the foot to move each structure due to contact between the first end of each structure and the diaphragm. Each structure is limited in its movement toward the foot by contact between the second end of the structure and the foot. The method further includes detecting a change in position of each structure relative to an initial position of each structure before the diaphragm was inflated, and measuring a shape of the foot based upon the change in position of each structure.

As discussed above, the measurement structures are preferably elongated gauge pins used in conjunction with a circuit board having a plurality of sensors, each of which corresponds to a single gauge pin and senses a selected area of each gauge pin to determine a position of each gauge pin. In another embodiment, the method includes determining the initial position of each structure prior to inflating the diaphragm, followed by comparing the initial position of each structure with a position of each structure after the diaphragm is inflated and each structure stops moving do to restrictions caused by the inflated diaphragm and by the foot.

The method described above may be performed a single time to measure the shape of the foot, or may be performed multiple times on the foot. A single measurement would be useful to save time in taking a measurement of the shape of the foot. Multiple measurements can also be performed in relatively quick succession to ensure that the measurement is accurate, and/or to determine whether the foot moved during measurement.

Figure 2:
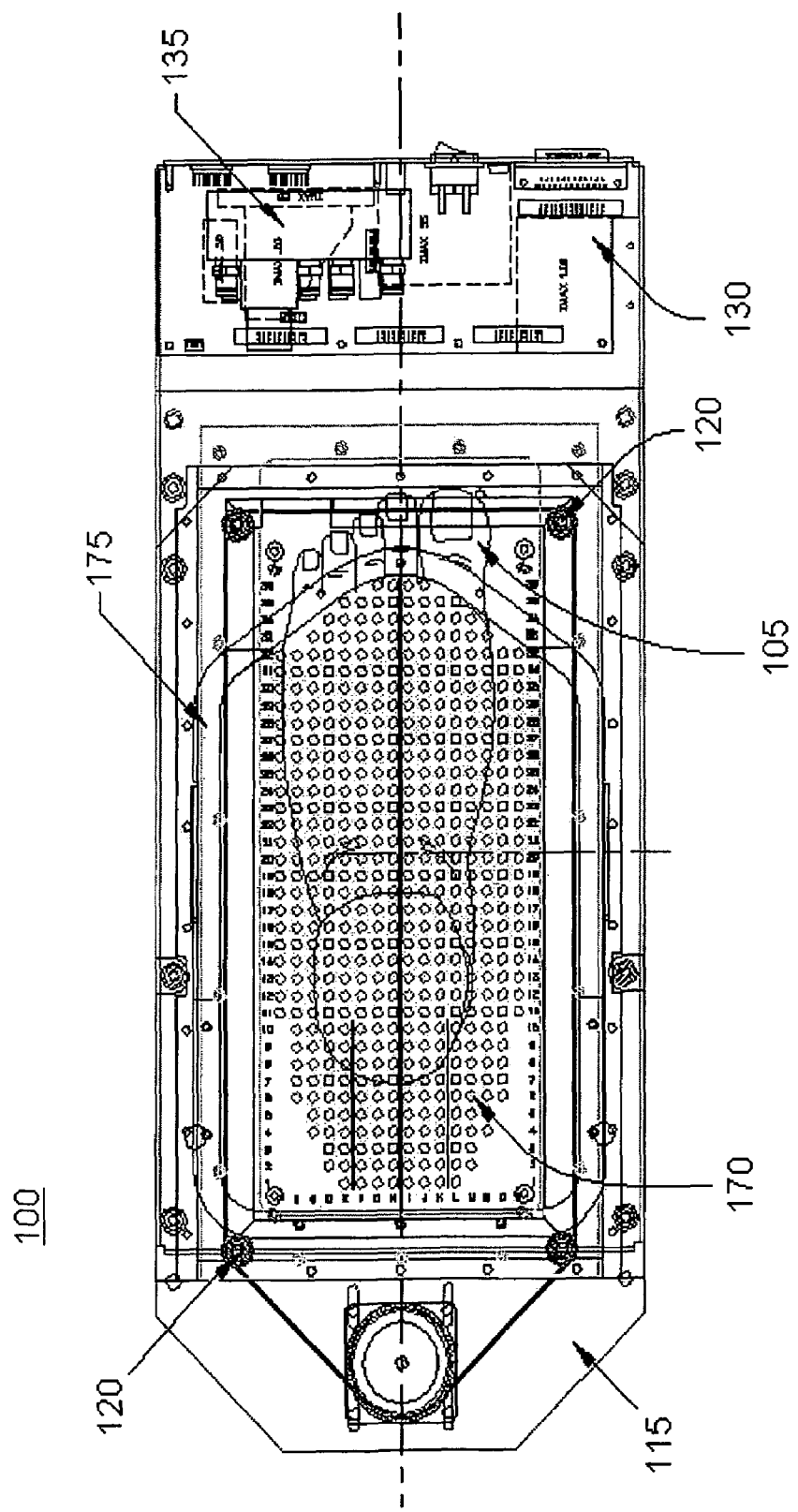
FIG. 2 is a top view of the measurement system shown in FIG. 1.
Figure 3:
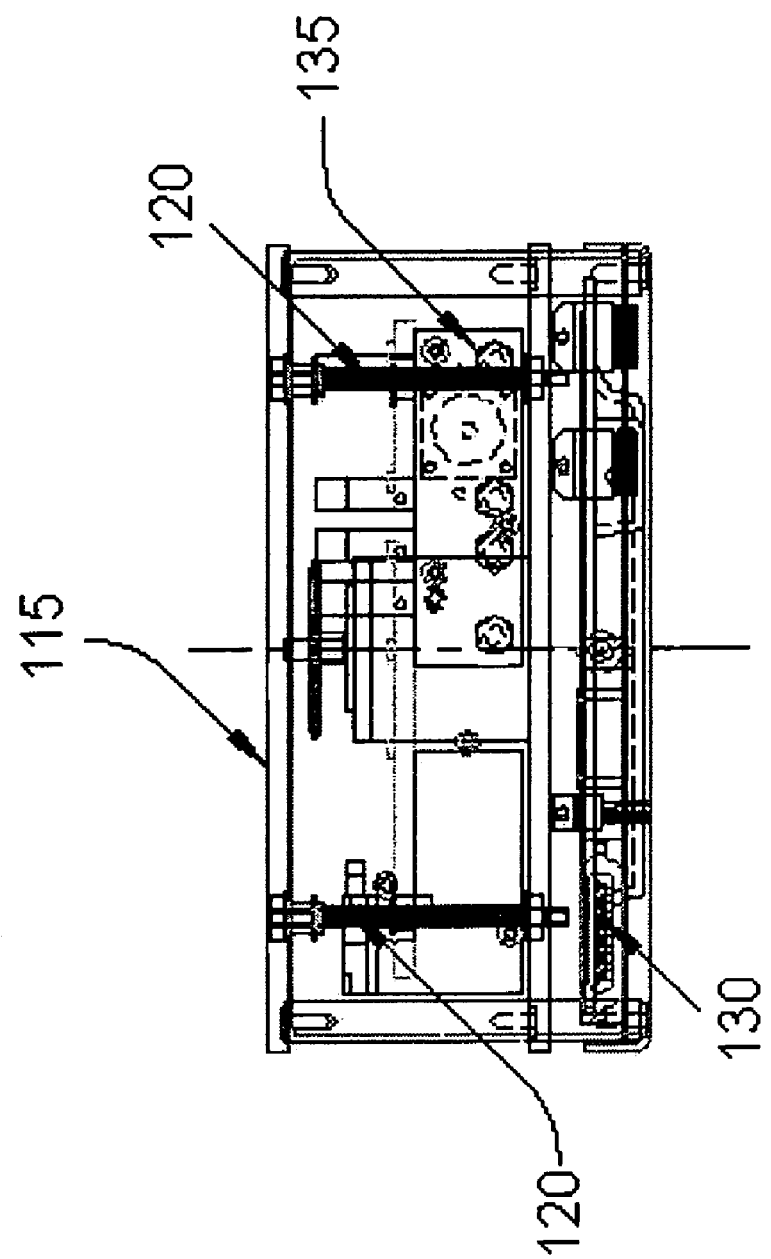
FIG. 3 is a front view of the measurement system shown in FIG. 1.

FIG. 1 is a side view of a system for measuring the contour of an object. FIG. 2 is a top view of the measurement system shown in FIG. 1. FIG. 3 is a front view of the measurement system shown in FIG. 1.

A system 100 for measuring the contours of an object, such as a foot 105, is shown in FIGS. 1-3. System 100 includes an electrostatic scanning matrix circuit board 110, a reference top surface 115, leadscrews 120, gauge pins 125, control electronics 130, an air controller 135, an air cavity 140, and a top protective diaphragm 145.

Reference top surface 115 is the mechanical zero elevation for the scanning mechanism as well as the top structural member of the scanner. Top surface 115 includes a series of holes 170 corresponding to each of gauge pins 125 so that gauge pins 125 can be advanced vertically from top surface 115 toward the contour of foot 105. Locating rib 150 is located on top surface 115 to assist subject in locating foot 105 in a lengthwise direction.

Top diaphragm 145 protects electronic components such as circuit board 110 from contamination. Top diaphragm 145 is preferably fabricated from a stretchable, flexible material, such as latex, rubber or other rubber-like materials.

Top diaphragm 145 is preferably attached to a diaphragm clamp 175 so that top diaphragm 145 is secured to system 100. Diaphragm clamp 175 extends around at least an area encompassing holes 170 so that contaminants cannot penetrate system 100 and contaminate sensitive components such as circuit board 110. Diaphragm clamp 175 is attached to top surface 115 such as by an adhesive, screws or clamps. As shown in FIG. 1, at least a portion of diaphragm clamp is elevated above top surface 115, so that top diaphragm 145 does not restrict gauge pins 125. Top diaphragm 145 may extend from the sides of elevated diaphragm clamp 175, or a sidewall may be included to prevent contaminates from entering system 100.

Each of gauge pins 125 include a reference area 155. Reference area 155 may be an area coated with a metallic material such as metal foil. Circuit board 110 includes sensors for detecting reference area 155 on each gauge pin 125.

Air cavity 140 includes a rigid lower half 160 and a preferably highly compliant diaphragm top 165 that urges gauge pins 125 upwards when air is introduced into cavity 140. Air controller 135, such as an air compressor, is provided to introduce air into cavity 140.

Leadscrews 120 are provided for translating circuit board 110 in an up/down direction to determine relative heights of each gauge pin 125 above top surface 115, based on a relative position of each reference area 155.

In use, subject foot 105 is placed on reference top surface 115, taking reasonable care to be in the approximate center. Locating rib 150 may be used to assist in positioning foot 105 properly on top surface 115.

Air controller 135 is activated to introduce air into air cavity 140, which in turn forces gauge pins 125 upward. Each gauge pin 125 contacts a different point on the contour of foot 105, and the upward motion of each gauge pin is inhibited by the contour surface of foot 105. Leadscrews 120 are activated to urge circuit board 110 upward and measure the relative position of each reference area 155. Preferably, control electronics 130 activate and control air controller 135, leadscrews 120 and circuit board 110 to acquire a measurement of the contour of foot 105. The position information may then be sent to a processor to be used for creating a digital impression of the contour of foot 105.

The method can be initiated by a user, for example, by activating a "Scan" macro. In response, the system will automatically perform the following steps: a) activate air controller 135 to activate and inflate diaphragm 165, b) optionally activate a locking mechanism to lock the gauge pins in place, c) activate the measurement device to take a measurement of the foot, and d) deactivate air controller 135 and diaphragm 165, and if applicable, deactivate the locking mechanism.

Nothing in this disclosure should be construed as limited to any specific method of mechanical or electromechanical measurement, or any specific measurement tool such as gauge pins. The improvements provided by the present invention may be utilized with any measurement technique that make it more practical in a retail oriented use. Furthermore, the present invention can be utilized to measure any object that can be placed on the support surface. The present invention is not limited to measuring feet.

It should be understood that various alternatives, combinations and modifications of the teachings described herein could be devised by those skilled in the art. The present invention is intended to embrace all such alternatives, modifications and variances that fall within the scope of the appended claims.

What is claimed is:

1. A foot measuring system comprising: a support surface for a foot; a plurality of movable measurement structures, wherein each structure of said plurality of movable structures has a first end and a second end; an inflatable diaphragm for contacting said first end of each said structure and forcing a movement of each said structure from an initial position toward a measurement position; a protective diaphragm located at or near said surface that prevents contamination of said system when said foot is placed on said surface, yet does not restrict said movement of said plurality of structures beyond said surface; and a measurement device for measuring said measurement position relative to said initial position of each said structure, after said movement of each said structure, to determine a shape of said foot.

2. The system of claim 1, wherein said movable structures are elongated pins oriented in a direction perpendicular to a plane of said support surface.

3. The foot measuring system of claim 1, wherein said support surface includes a plurality of holes through which said second end of each of said structures can be advanced toward said foot.

4. The system of claim 1, wherein said movement of each said structure is restricted by contact between said second end and said foot.

5. The system of claim 1, wherein said measurement device includes a plurality of sensors that sense a selected area of each said structure to determine a relative change between said measurement position and said initial position of each said structure after said diaphragm is inflated.

6. The system of claim 5, wherein said plurality of sensors are positioned in an array on a circuit board, and wherein said selected area is a metalized area detectable by a respective sensor of said plurality of sensors.

7. The system of claim 5, wherein said measurement device performs said measurement once or multiple times to determine said shape of said foot.

8. The system of claim 5, further comprising a processor operatively connected to said plurality of sensors, wherein said processor: determines said initial position of each said structure prior to inflating said diaphragm; compares said initial position of each said structure with said measurement position of each said structure after said diaphragm is inflated and each said structure stops moving do to restrictions caused by said inflated diaphragm and by said foot; and constructs a digital impression based on said change of position of each said structure.

9. The system of claim 1, further comprising: a bottom surface in a substantially airtight connection with at least a portion of said diaphragm to form an airtight cavity bounded by said bottom surface and said diaphragm; and an air controller to introduce air into said cavity, wherein introducing air into said cavity applies a force to each said structure by said diaphragm to force said movement of each said structure toward said foot.

10. The system of claim 1, wherein said protective diaphragm is made from a stretchable and flexible material.

11. The system of claim 1, further comprising a ridge on said support surface to aid in properly positioning said foot on said support surface.

12. The system of claim 1, further comprising a device to selectively restrict said movement of one or more of said plurality of measurement structures.

13. A method for measuring the contours of a foot, comprising: placing said foot against a support surface of a foot measuring system; inflating a diaphragm to force a plurality of movable measurement structures through said surface and toward said foot, wherein each structure of said plurality of movable structures has a first end and a second end; moving each said structure due to contact between said first end of each said structure and said diaphragm, wherein each said structure is limited in movement by contact between said second end and said foot; detecting a change in position of each said structure relative to an initial position of each said structure; and measuring a shape of said foot based upon said change in position of each said structure, wherein said foot measuring system further includes a protective diaphragm located at or near said surface that prevents contamination of said system when said foot is placed on said surface, yet does not restrict a movement of said plurality of structures beyond said surface.

14. The method of claim 13, wherein said movable structures are elongated pins oriented in a direction perpendicular to a plane of said support surface.

15. The method of claim 13, wherein said support surface includes a plurality of holes through which said second end of each of said structures is advanced toward said foot.

16. The method of claim 13, further comprising: including a plurality of sensors that sense a selected area of each said structure; and determining said initial position of each said structure prior to inflating said diaphragm.

17. The method of claim 16, wherein said plurality of sensors are positioned in an array on a circuit board, and wherein said selected area is a metalized area detectable by a respective sensor of said plurality of sensors.

18. The method of claim 13, wherein detecting said change in position is accomplished by: comparing said initial position of each said structure with a position of each said structure after said diaphragm is inflated and each said structure stops moving due to restrictions caused by said inflated diaphragm and by said foot.

19. The method of claim 18, wherein measuring said shape of said foot includes constructing a digital impression based on said change of position of each said structure.

20. The method of claim 13, wherein at least a portion of said diaphragm forms an airtight cavity bounded by a bottom surface, and wherein said diaphragm is inflated by introducing air into said cavity.

21. The method of claim 13, wherein said method is performed once or multiple times to determine said shape of said foot.

* * * * *